US007754888B2

(12) United States Patent
Loso et al.

(10) Patent No.: US 7,754,888 B2
(45) Date of Patent: Jul. 13, 2010

(54) INSECTICIDAL N-SUBSTITUTED (HETEROARYL)ALKYL SULFILIMINES

(75) Inventors: Michael R. Loso, Carmel, IN (US); Benjamin M. Nugent, Brownsburg, IN (US); Yuanming Zhu, Carmel, IN (US); Richard B. Rogers, Mobile, AL (US); Jim X. Huang, Carmel, IN (US); James M. Renga, Indianapolis, IN (US); Zoltan L. Benko, Indianapolis, IN (US); Gregory T. Whiteker, Carmel, IN (US); John F. Daeuble, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 408 days.

(21) Appl. No.: 11/705,185

(22) Filed: Feb. 9, 2007

(65) Prior Publication Data

US 2008/0280915 A1 Nov. 13, 2008

Related U.S. Application Data

(60) Provisional application No. 60/841,934, filed on Sep. 1, 2006.

(51) Int. Cl.
*C07D 213/00* (2006.01)
*C07D 237/00* (2006.01)
*C07D 239/02* (2006.01)
*C07D 241/00* (2006.01)

(52) U.S. Cl. .................. 546/338; 544/224; 544/335; 544/336

(58) Field of Classification Search .................. 546/338; 544/224, 335, 336
See application file for complete search history.

(56) References Cited

U.S. PATENT DOCUMENTS 4,053,622 A * 10/1977 Kollmeyer .................. 514/385
2005/0228027 A1 10/2005 Zhu et al.

FOREIGN PATENT DOCUMENTS

WO PCT/US2007/003787 2/2008
WO PCT/US2007/003787 10/2008

OTHER PUBLICATIONS

F Zaragoza Dorwald Side Reactions in Organic Synthesis 2005, Wiley-VCH.*
U.S. Appl. No. 11/704,397, filed Feb. 9, 2007, Jim X. Huang, et al.
U.S. Appl. No. 11/704,756, filed Feb. 9, 2007, Kim E. Arndt, et al.
U.S. Appl. No. 11/704,759, filed Feb. 9, 2007, Stephen T. Heller, et al.
U.S. Appl. No. 11/704,796, filed Feb. 9, 2007, Kevin G. Meyer, et al.
U.S. Appl. No. 11/704,797, filed Feb. 9, 2007, Michael R. Loso, et al.
U.S. Appl. No. 11/704,820, filed Feb. 9, 2007, Yuanming Zhu, et al.
U.S. Appl. No. 11/704,824, filed Feb. 9, 2007, Jim X. Huang, et al.
U.S. Appl. No. 11/704,825, filed Feb. 9, 2007, James M. Renga, et al.
U.S. Appl. No. 11/704,842, filed Feb. 9, 2007, Michael R. Loso, et al.
U.S. Appl. No. 11/704,853, filed Feb. 9, 2007, Michael R. Loso, et al.
Konig, Wolfgang; Geiger, Rolf; and Siedel, Walter; "Neue S-Schutzgruppen fur Cystein;" Chem. Ber. 101, pp. 681-693 (1968).
Bordwell, F.G. and Williams, Joel M., Jr.; "The Ramberg-Backlund Reaction of Benzyl α-Halobenzyl and Halomethyl Sulfones;" Journal of the American Chemical Society, 90:2, pp. 435-439, Jan. 1, 1968.
Marchand, E.; Morel, G.; and Foucaud, A; "A Convenient Method for the Sulfenylation of Nitriles;" Synthesis, May 1978, pp. 360-361, Georg Thieme Publishers.
Wladislaw, B.; Marzorati, L.; Uchoa, R.B.; and Viertler, H.; "Some New α-Monosulfenylated Benzyl Phenyl Sulfones; Versatile Intermediates for the Synthesis of p-Substituted Benzaldehydes;" Synthesis, May 1985, pp. 553-555.
Reglier, Marius and Julia, Sylvestre A.; "On the Properties of Some Substituted $\alpha^1$-Lithiated a(Z), Y-Butadienyl Sulfides: Cyclisations and Rearrangements;" Tetrahedron Letters, vol. 26, No. 19, pp. 2319-2322, 1985, Pergamon Press Ltd.
Wnuk, Stanislaw F. and Robins, Morris J.; "Antimony(III) Chloride Exerts Potent Catalysis of the Conversion of Sulfoxides to α-Fluoro Thioethers with (Diethylamino)sulfur Trifluoride;" J. Org Chem. 1990, 55, pp. 4757-4760, American Chemical Society.
Holoboski, Mark A. and Koft, Emil; "Asymmetric Synthesis of the Milbemycin β3 Spiroketal Subunit;" J. Org. Chem, 1992, 57, pp. 965-969, American Chemical Society.
Tavares, Francis X.; Deaton, David N.; Miller, Larry R.; and Wright, Lois L.; "Ketoamide-Based Inhibitors of Cysteine Protease, Cathepsin K: P3 Modifications;" J. Med. Chem. 2004, 47, pp. 5057-5068, American Chemical Society.
Streiff, Stephane; Ribeiro, Nigel; and Desaubry, Laurent; "Synthesis of Allysilanes by Reductive Lithiation of Thioethers;" J. Org. Chem. 2004, 69, pp. 7592-7598, American Chemical Society.
Cheng, Heng; Chong, Youhoon; Hwang, Inkyu; Tavassoli, Ali; Zhang, Yan; Wilson, Ian A.; Benkovic, Stephen J.; and Boger, Dale L.; "Design, synthesis, and biological evaluation of 10-methanesulfonyl-DDACTHF, 10-methanesulfony1-5-DACTHF, and 10-methylthio-DDACTHF as potent inhibitors of GAR Tfase and the de novo purine biosynthetic pathway;" Biorganic & Medicinal Chemistry 13, 2005, pp. 3577-3585, Elsevier Ltd.
Zhu, Gui-Dong; Gong, Jianchun; Claiborne, Akiyo; Woods, Keith W.; Gandhi, Viraj B.; Thomas, Sheela; Luo, Yan; Liu, Xuesong; Shi, Yan; Guan, Ran; Magnone, Shayna R.; Klinghofer, Vered; et al.; "Isoquinoline-pyridine-based protein kinase B/Akt antagonists: SAR and in vivo antitumor activity;" Biorganic & Medicinal Chemistry Letters 16, 2006, pp. 3150-3155, Elsevier Ltd.
Suga, Seiji; Matsumoto, Kouichi; Ueoka, Koji; and Yoshida, Jun-Ichi; "Indirect Cation Pool Method. Rapid Generation of Alkoxycarbenium Ion Pools from Thioacetals;" J. Am. Chem. Soc., 2006, 128, pp. 7710-7711, American Chemical Society.

* cited by examiner

*Primary Examiner*—Rita J Desai
*Assistant Examiner*—John Mabry
(74) *Attorney, Agent, or Firm*—Carl D. Corvin; Craig E. Mixan

(57) ABSTRACT

N-Substituted (heteroaryl)alkyl sulfilimines are effective at controlling insects.

8 Claims, No Drawings

INSECTICIDAL N-SUBSTITUTED (HETEROARYL)ALKYL SULFILIMINES

This application claims the benefit of U.S. Provisional Application Ser. No. 60/841,934 filed on Sep. 1, 2006.

BACKGROUND OF THE INVENTION

The present invention concerns novel N-substituted (heteroaryl)alkyl sulfilimines and their use in controlling insects, particularly aphids and other sucking insects, as well as certain other invertebrates. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

SUMMARY OF THE INVENTION

This invention concerns compounds useful for the control of insects, especially useful for the control of aphids and other sucking insects. More specifically, the invention concerns compounds of the formula (I)

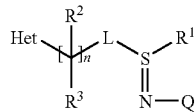

wherein
Het represents:

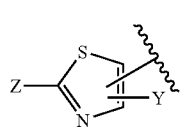 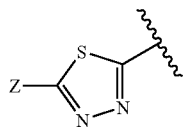

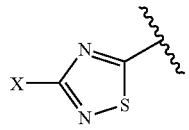 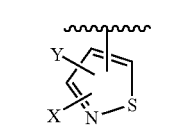

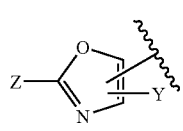 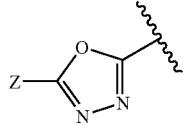

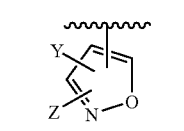

-continued

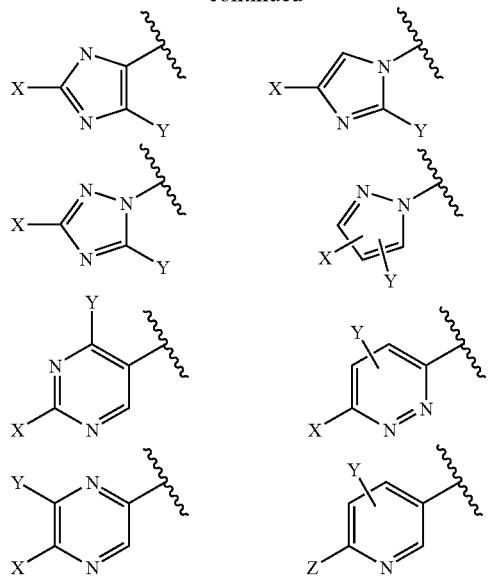

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^6$ where m is an integer from 0-2, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^1$ where m is an integer from 0-2, $COOR^4$, $CONR^4R^5$, aryl or heteroaryl;

Z represents $C_1$-$C_4$ haloalkyl, $C_2$-$C_4$ alkenyl, $C_2$-$C_4$ alkynyl, $C_2$-$C_4$ haloalkenyl, $C_1$-$C_4$ haloalkoxy, CN, $NO_2$, $SO_mR^1$ where m is an integer from 0-2, $COOR^4$ or $CONR^4R^5$;

n is an integer from 0-3;

L represents either a single bond, —$CH_2$—, or —$CH(CH_2)_p$— where p is an integer from 1-3 and either $R^1$, S and L or $R^2$, L and the common carbon to which they attach are taken together to represent a 4-, 5-, or 6-membered ring with up to, but no more than, 1 heteroatom;

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl, heteroarylalkyl, or, alternatively, is taken together with either L or $R^2$ to form a saturated 4-, 5-, or 6-membered ring;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, $COOR^4$, $CONR^4R^5$, arylalkyl, heteroarylalkyl, or, alternatively, $R^2$ and $R^3$ and the common carbon to which they attach form a 3-6 membered ring, or $R^2$ and $R^1$ taken together form a saturated 4-, 5-, or 6-membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloakenyl, aryl, heteroaryl, arylalkyl or heteroarylalkyl;

$R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl, heteroarylalkyl; and Q represents $NO_2$ or CN.

Preferred compounds of formula (I) include the following classes:

(1) Compounds of formula (I) wherein Het is (6-substituted)pyridine-3-yl or (2-substituted)thiazol-5-yl and where Z is $C_1$-$C_2$ haloalkyl and Y is hydrogen;

(2) Compounds of formula (I) wherein $R^2$ and $R^3$ are as previously defined, $R^1$ is methyl, n is 1, and L is a single bond, having the structure:

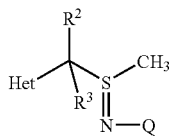

(3) Compounds of formula (I) wherein n is 1, $R^1$, S and L taken together form a standard 4-, 5-, or 6-membered ring such that L is —CH(CH$_2$)$_p$—, and $R^1$ is —CH$_2$— having the structure:

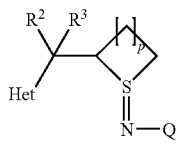

(4) Compounds of formula (I) wherein n is 0, $R^1$, S and L taken together form a standard 4-, 5-, or 6-membered ring such that L is —CH(CH$_2$)$_p$—, and $R^1$ is —CH$_2$— having the structure:

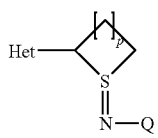

(5) Compounds of formula (I) where Q is CN;

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methyl-ethyl, propyl, 1,1-dimethylethyl, and cyclopropyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo" includes fluorine, chlorine, bromine and iodine, with fluorine being preferred.

The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$OC(O)alkyl, $C_1$-$C_6$ NHC(O)alkyl, C(O)OH, $C_1$-$C_6$ C(O)Oalkyl, C(O)NH$_2$, $C_1$-$C_6$ C(O)NHalkyl, or $C_1$-$C_6$ C(O)N(alkyl)$_2$, provided that the substituents are sterically compatible and the rules of chemical bonding and strain energy are satisfied.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (I), wherein Q is NO$_2$ and $R^1$, $R^2$, $R^3$, n, and L are as previously defined can be prepared by the method illustrated in Scheme A.

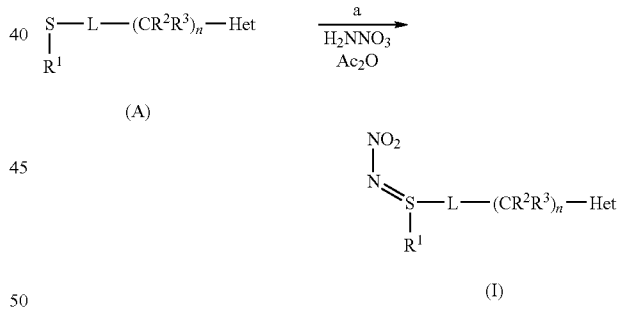

In step a of Scheme A, sulfide of formula (A) is reacted with nitramide in the presence of acetic anhydride to provide the sulfilimine (I). (Shitov, O. P.; Seleznev, A. P; Tartakovski, V. A. Inst. Org. Kim. im. Zelinskogo, Moscow, USSR. Izvestiya Akademii Nauk SSSR, Seriya Khimicheskaya (1991), (5), 1237-8.)

The compounds of formula (Ia), wherein Q is CN and Het, $R^1$, $R^2$, $R^3$, n, and L are as previously defined can be prepared by the method illustrated in Scheme B. Accordingly, the precursor sulfide is oxidized with iodobenzene diacetate in the presence of cyanamide at 0° C. to give sulfilimine (Ia). The reaction can be carried out in a polar aprotic solvent like CH$_2$Cl$_2$.

Scheme B

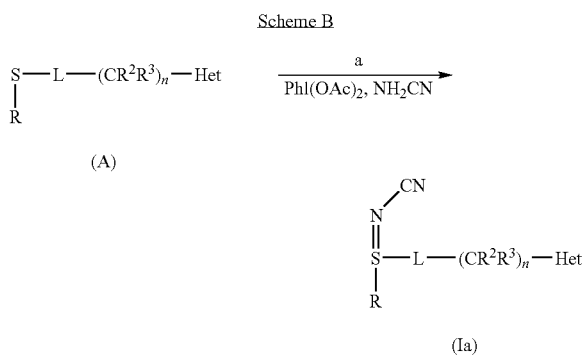

The precursor sulfides (A) can, in turn, be prepared in different ways as illustrated in Schemes C, D, E, F and G.

In Scheme C, the sulfide of formula (A₁), wherein L is a single bond, n is 1, R³=H, and R¹, R² and Het are as previously defined can be prepared from halides of formula (D) by nucleophilic substitution with the sodium salt of an alkyl thiol.

Scheme C

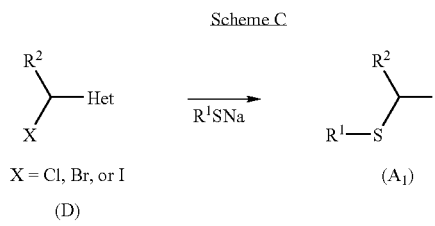

In Scheme D, the sulfide of formula (A₂), wherein L is a single bond, n is 3, R³=H, and R¹, R² and Het are as previously defined, can be prepared from the chloride of formula (E) by reacting with a 2-mono substituted methyl malonate in the presence of base such as potassium tert-butoxide to provide 2,2-disubstituted malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme D

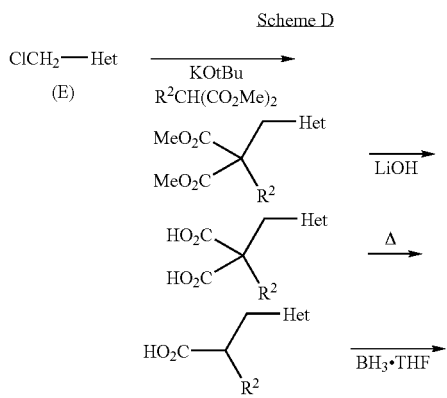

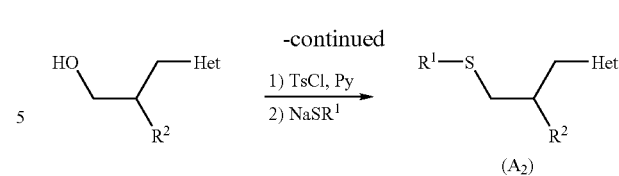

In Scheme E, the sulfide of formula (A₃), wherein L is a single bond, n is 2, R³=H, and R¹, R² and Het are as previously defined, can be prepared from the nitrile of formula (F) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

Scheme E

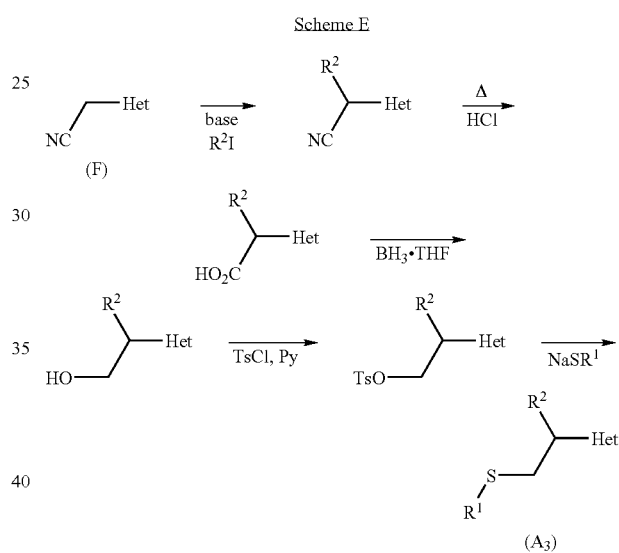

In Scheme F, the sulfide of formula (A₄), wherein n is 0, R¹ is —CH₂—, L is —CH(CH₂)$_p$— where p is either 2 or 3 and, taken together with R¹, S and L form a 5- or 6-membered ring, and Het is as previously described can be prepared from tetrahydrothiophene (p=2) or pentamethylene sulfide (p=3) (G). Chlorination of the cyclic sulfide starting material with N-chlorosuccinimide in benzene followed by alkylation with certain lithiated heterocycles or Grignard reagents can lead to the desired sulfides (A₄) in satisfactory yield.

Scheme F

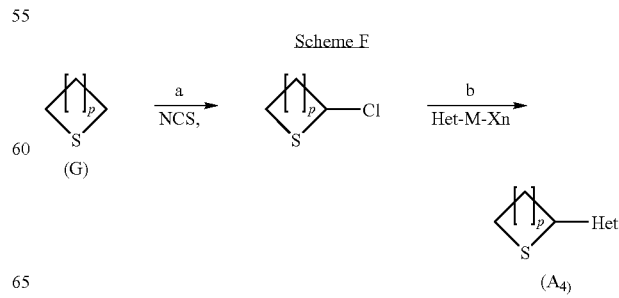

A more efficient protocol to access cyclic sulfides of formula (A$_4$) is illustrated in Scheme G where Het is a 6-substituted pyridin-3-yl and Z is previously defined. Accordingly, reduction with sodium borohydride, chlorination with thionyl chloride, and nucleophilic substitution with the sodium salt of an alkyl thiol provides desired sulfides (A$_1$).

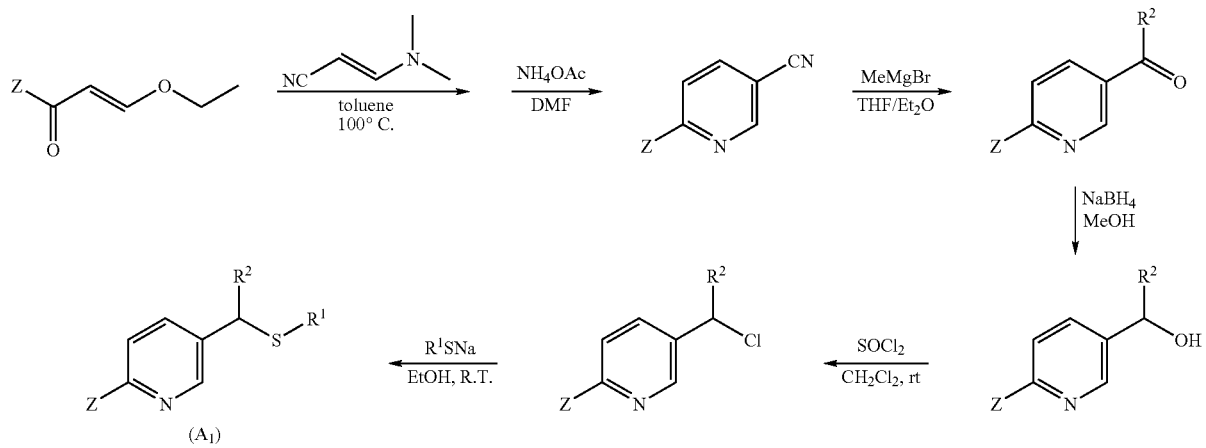

thiourea is added to a substituted chloromethyl pyridine, which, after hydrolysis, and alkylation with the appropriate bromo chloroalkane (p=1, 2, or 3) under aqueous base conditions, yields sulfide (H). Subsequent cyclization of (H) in the presence of a base like potassium-t-butoxide in a polar aprotic solvent such as THF provides cyclic sulfide (A$_4$).

A variation of Scheme H is illustrated in Scheme I, wherein enamines, formed from the addition of an amine, e.g., pyrrolidine, with the Michael adduct of certain sulfides with appropriately substituted α,β-unsaturated aldehydes, are coupled with substituted enones and cyclized with ammonium acetate in CH$_3$CN to yield the desired sulfides (A$_1$) wherein R$^1$, R$^2$, R$^3$, and Z are previously defined.

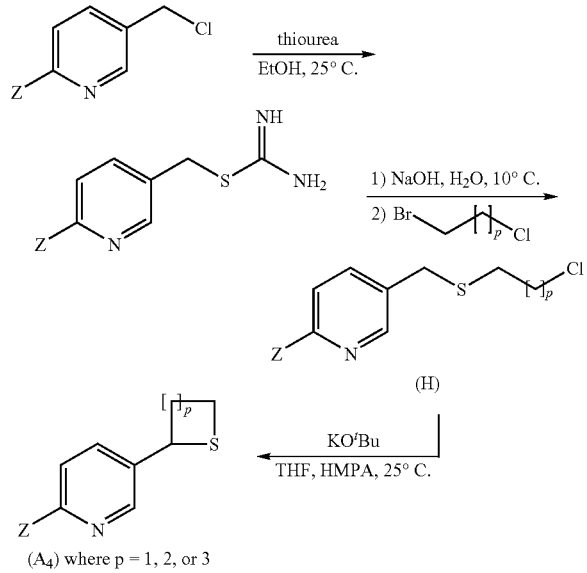

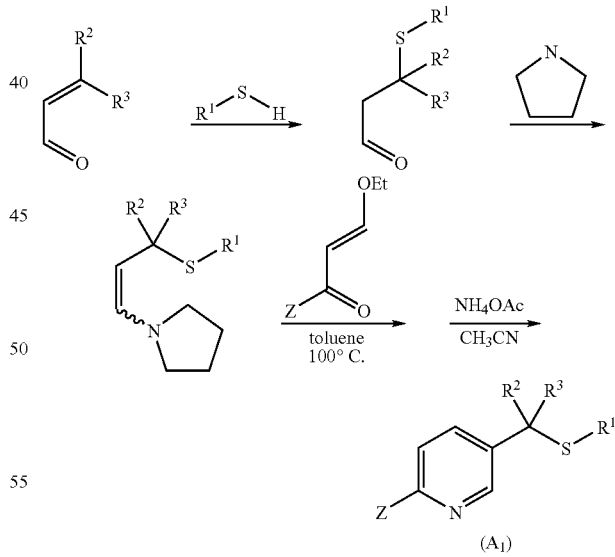

Certain sulfides of formula (A$_1$) wherein Het is a substituted pyridin-3-yl, Z is as previously defined, and R$^1$, R$^2$=CH$_3$ can be prepared alternatively via methods illustrated in Scheme H. Accordingly, the appropriate enone is coupled with dimethylaminoacrylonitrile and cyclized with ammonium acetate in DMF to yield the corresponding 6-substituted nicotinonitrile. Treatment with methyl-magnesium bromide, A variation of this method, illustrated in Scheme J, can be used to prepare cyclic pyridyl sulfides A$_5$ wherein n=1, L=—(CH$_2$)—, and R$^1$, R$^2$ connect to form a 5-membered ring. Accordingly, reaction of tetrahydrothiophen-3-one with triphenylphosphine and dimethyl-carbonate provides the corresponding olefin, which is then hydroformylated with hydrogen and carbon monoxide in the presence of a rhodium catalyst at elevated pressure to afford aldehyde (N). Remaining steps to convert the aldehyde to sulfide ($A_5$) follows the same protocol as previously described in Scheme I.

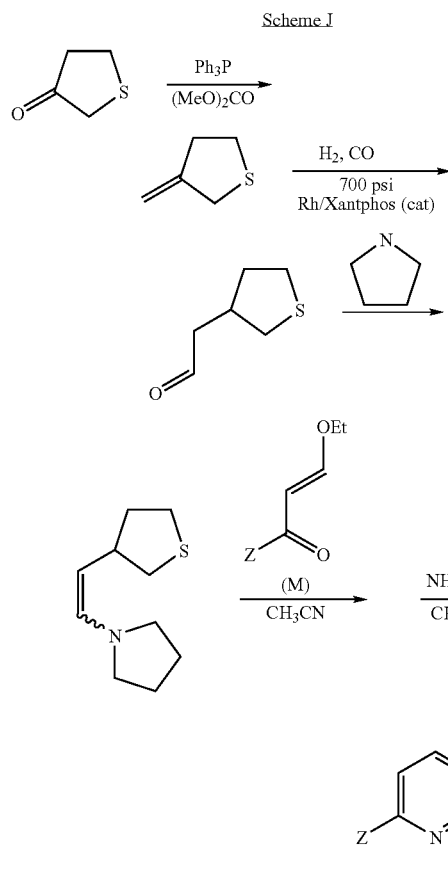

Scheme J

In Scheme K sulfides of formula ($A_6$) wherein $R^1$ and Z are as previously defined, n=1 and L, $R^2$, and the common carbon they connect to are taken together to form a 4-, 5-, or 6-membered ring (x=0-2) can be prepared from 2-substituted 5-bromo-pyridines via a halogen metal exchange with either isopropyl Grignard or n-butyl lithium followed by addition to cyclic ketone such as cyclopentanone (x=1), dehydration to the olefin under acidic conditions, hydroboration (borane in tetrahydrofuran), oxidative cleavage (sodium hydroxide and hydrogen peroxide), conversion of the resulting alcohol to a easily displaceable moiety such as a methanesulfonyl group (by treatment with methanesulfonyl chloride and triethyl amine), and finally nucleophilic substitution with the sodium salt of an alkyl thiol.

Scheme K

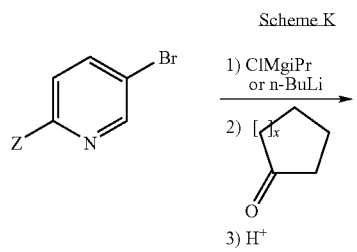

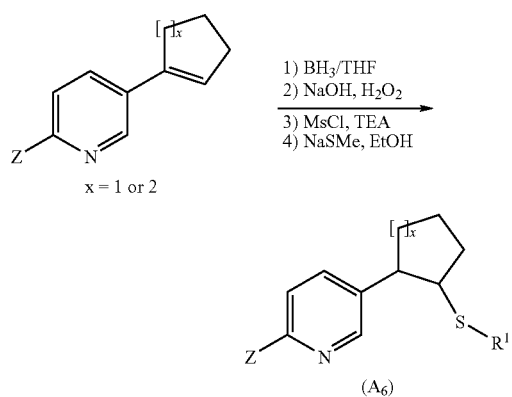

EXAMPLES

Example I

Preparation of {1-[6-(trifluoromethyl)pyridin-3-yl]methyl}(methyl)-$\lambda^4$-sulfanylidenecyanamide (1)

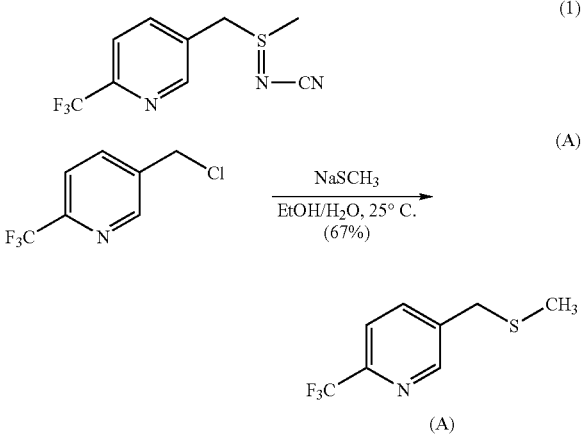

To a solution of 3-chloromethyl-6-(trifluoromethyl)pyridine (5.1 g, 26 mmol) in dimethyl sulfoxide (DMSO; 20 mL) was added sodium thiomethoxide in one portion (1.8 g, 26 mmol). A violent exothermic reaction was observed which resulted in the reaction turning dark. The reaction was stirred for 1 hr, then additional sodium thiomethoxide (0.91 g, 13 mmol) was added slowly. The reaction was stirred overnight, after which it was poured into $H_2O$ and several drops of conc. HCl were added. The mixture was extracted with $Et_2O$ (3×50 mL) and the organic layers combined, washed with brine, dried over $MgSO_4$, filtered, and concentrated. The crude product was purified by chromatography (Prep 500, 10% acetone/hexanes, v/v) to furnish the sulfide (A) as a pale yellow oil (3.6 g, 67%). $^1$H NMR (300 MHz, $CDCl_3$) δ 8.6 (s, 1H), 7.9 (d, 1H), 7.7 (d, 1H), 3.7 (s, 2H), 2.0 (s, 3H); GC-MS: mass calcd for $C_8H_8F_3NS$ $[M]^+$ 207. Found 207.

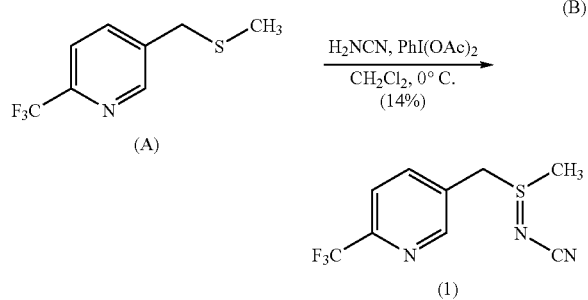

To a solution of sulfide (A) (3.5 g, 17 mmol) and cyanamide (1.4 mg, 34 mmol) in $CH_2Cl_2$ (30 mL) at 0° C. was added iodobenzenediacetate (11.0 g, 34 mmol) all at once. The reaction was stirred for 30 min and then allowed to warm to room temperature overnight. The mixture was diluted with $CH_2Cl_2$ (50 mL) and washed with $H_2O$. The aqueous layer was extracted with ethyl acetate (4×50 mL), and the combined $CH_2Cl_2$ and ethyl acetate layers dried over $MgSO_4$ and concentrated. The crude product was triturated with hexanes and purified by chromatography (chromatotron, 60% acetone/hexanes, v/v) to furnish the sulfilimine (1) as a yellow gum (0.60 g, 14%). IR (film) 3008, 2924, 2143, 1693 $cm^{-1}$; $^1$H NMR (300 MHz, $CDCl_3$) δ 8.8 (s, 1H), 8.0 (d, 1H), 7.8 (d, 1H), 4.5 (d, 1H), 4.3 (d, 1H), 2.9 (s, 3H); LC-MS (ESI): mass calcd for $C_9H_9F_3N_3S$ $[M+H]^+$ 248.04. Found 248.

Example II

Preparation of (1-{6-[chloro(difluoro)methyl]pyridin-3-yl}ethyl)(methyl)-$\lambda^4$-sulfanylidenecyanamide (2)

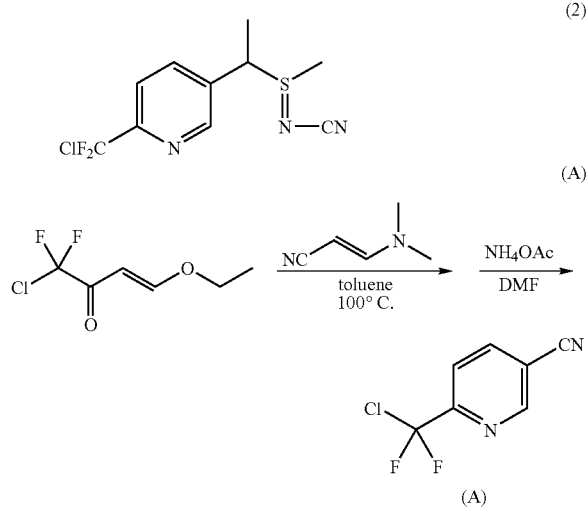

(3E)-1-Chloro-4-ethoxy-1,1-difluorobut-3-en-2-one (7.36 g, 40 mmol) was dissolved in dry toluene (40 mL) and treated with 3-dimethylaminoacrylonitrile (4.61 g, 48 mmol) at room temperature. The solution was heated at about 100° C. for 3.5 hr. The solvent was then removed under reduced pressure and the remaining mixture was re-dissolved in dimethyl formamide (DMF; 20 mL), treated with ammonium acetate (4.62 g, 60 mmol) and stirred at room temperature overnight. Water was added to the reaction mixture and the resulting mixture was extracted with ether-$CH_2CH_2$ (1:2, v/v) twice. The combined organic layer was washed with brine, dried, filtered and concentrated. The residue was purified on silica gel to give 3.1 g of 6-[chloro(difluoro)methyl]nicotinonitrile (A) as light colored oil in 41% yield. GC-MS: mass calcd for $C_7H_3ClF_2N_2$ $[M]^+$ 188. Found 188.

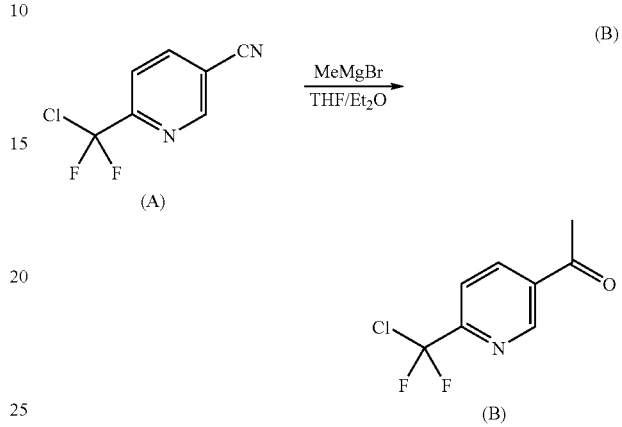

6-[Chloro(difluoro)methyl]nicotinonitrile (A) (3.0 g, 15.8 mmol) was dissolved in anhydrous ether (25 mL) and cooled in an ice-water bath. A solution of 3 M of methylmagnesium bromide in hexane (6.4 mL, 19 mmol) was added through a syringe. After the addition was over, the mixture was stirred at 0° C. for 5 hr and then at room temperature for 10 hr. The reaction was quenched slowly with 1 N citric acid aqueous solution at 0° C. and the resulting mixture was stirred at room temperature for 1 hr. The pH was adjusted back to pH 7 with saturated aqueous $NaHCO_3$ solution. The two phases were separated and the aqueous phase was extracted with ethyl acetate twice. The combined organic layer was washed with brine, dried over anhydrous $Na_2SO_4$, filtered, and concentrated. The remaining mixture was purified on silica gel eluted with 15% acetone in hexane (v/v) to give 0.88 g of the desired product 1-{6-[chloro(difluoro)methyl]pyridin-3-yl}ethanone (B) as brownish oil in 30% yield. GC-MS: mass calcd for $C_8H_6ClF_2NO$ $[M]^+$ 205. Found 205.

To a solution of 1-{6-[chloro(difluoro)methyl]pyridin-3-yl}ethanone (B) (0.85 g, 4.14 mmol) in MeOH (10 mL) at 0°

C. was added NaBH$_4$ (0.16 g, 4.14 mmol). The mixture was stirred for 30 min and 2 M HCl aqueous solution was added until pH reached 7. Solvent was removed under reduced pressure and the remaining mixture was extracted with CH$_2$Cl$_2$ (2×50 mL). The combined organic layer was dried over anhydrous Na$_2$SO$_4$, filtered, concentrated, and dried in vacuo to give 0.798 g of analytically pure 1-{6-[chloro(difluoro)methyl]-pyridin-3-yl}ethanol (C) on GC-MS as a light yellow oil in 93% yield. GC-MS: mass calcd for C$_8$H$_6$ClF$_2$NO [M]$^+$ 207. Found 207.

sure and the residue was re-taken into ether/CH$_2$Cl$_2$ and brine. The two phases were separated and the aqueous layer was extracted with CH$_2$Cl$_2$ one more time. The combined organic layer was dried over anhydrous Na$_2$SO$_4$, filtered, concentrated, and purified on silica gel using 5% ethyl acetate in hexane (v/v) to give 0.348 g of the 2-[chloro(difluoro)methyl]-5-[1-(methylthio)ethyl]pyridine (E) in 40% yield GC-MS: mass calcd for C$_9$H$_{10}$ClF$_2$NS [M]$^+$ 237. Found 237.

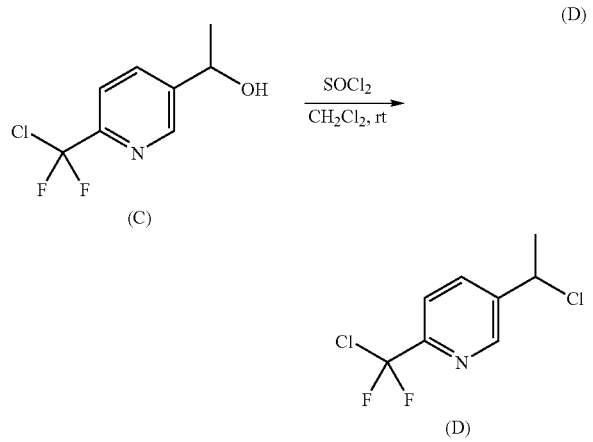

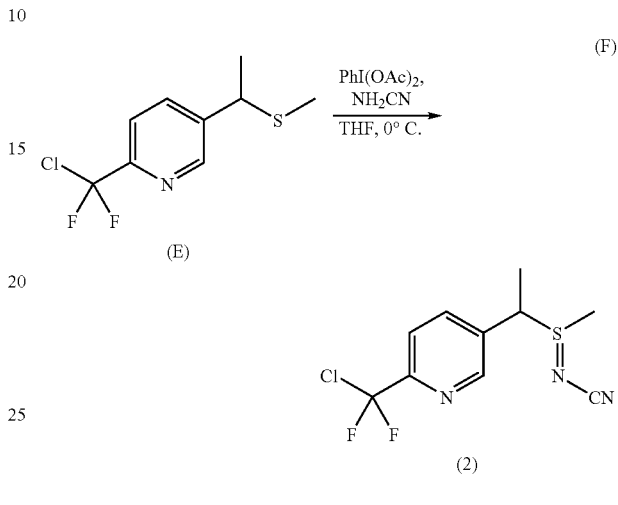

To a solution of 1-{6-[chloro(difluoro)methyl]pyridin-3-yl}ethanol (0.78 g, 3.77 mmol) in CH$_2$Cl$_2$ (40 mL) was added thionyl chloride (0.54 mL, 7.54 mmol) dropwise at room temperature. After 1 hr, the reaction was quenched slowly with saturated NaHCO$_3$ aqueous solution and the two phases were separated. The organic layer was dried over Na$_2$SO$_4$, filtered, concentrated, and dried in vacuum to give 0.83 g of the crude 2-[chloro(difluoro)methyl]-5-(1-chloroethyl)pyridine (D) as brown oil in 98% yield, which was directly used for the next step reaction. GC-MS: mass calcd for C$_8$H$_7$Cl$_2$F$_2$N [M]$^+$ 225. Found 225.

To a stirred solution of 2-[chloro(difluoro)methyl]-5-[1-(methylthio)-ethyl]pyridine (E) (0.32 g, 1.35 mmol) and cyanamide (0.058 g, 1.35 mmol) in tetrahydrofuran (THF; 7 mL) was added iodobenzene diacetate (0.44 g, 1.35 mmol) in one portion at 0° C. and the resulting mixture was stirred at this temperature for 1 hr and then at room temperature for 2 hr. The solvent was removed under reduced pressure and the resulting mixture was dissolved in CH$_2$Cl$_2$, washed with half-saturated brine, dried over anhydrous Na$_2$SO$_4$, filtered, concentrated, and purified on silica gel using 50% acetone in hexane (v/v) to give 0.175 g of (1-{6-[chloro-(difluoro)methyl]pyridin-3-yl}ethyl)(methyl)-λ$^4$-sulfanylidenecyanamide (2) as a light-yellow oil in 48% yield. $^1$H NMR (300 MHz, CDCl$_3$) δ 8.71 (d, J=1.8 Hz, 1H), 7.91 (dd, J=8.4, 1.8 Hz, 1H) 7.78 (d, J=8.4 Hz, 1H), 4.42 (q, J=6.9 Hz, 1H), 2.64 (s, 3H), 1.92 (d, J=6.9 Hz, 3H); LC-MS: mass calcd for C$_{10}$H$_{10}$ClF$_2$N$_3$S [M+1]$^+$ 278. Found 278.

Example III

Preparation of {1-[6-(trichloromethyl)pyridin-3-yl]ethyl}(methyl)-λ$^4$-sulfanylidenecyanamide (3)

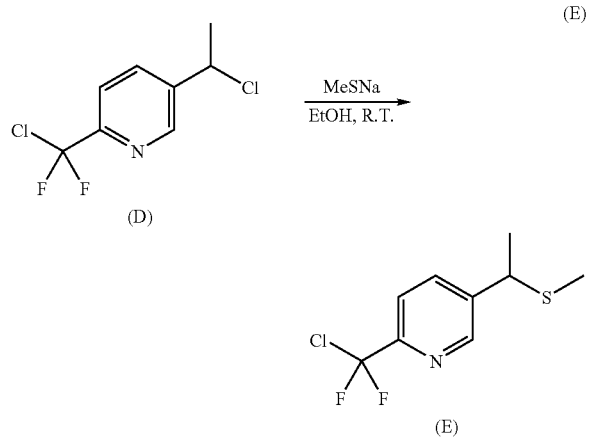

To a solution of 2-[chloro(difluoro)methyl]-5-(1-chloroethyl)pyridine (D) (0.81 g, 3.6 mmol) in ethanol (10 mL) was added sodium thiomethoxide (0.52 g, 7.4 mmol) under stirring in one portion at 0° C. After 10 min, the mixture was allowed to warm to room temperature and stirred overnight. The solvent ethanol was then removed under reduced pres-

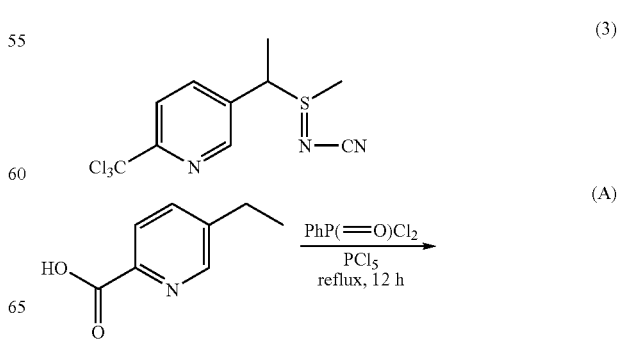

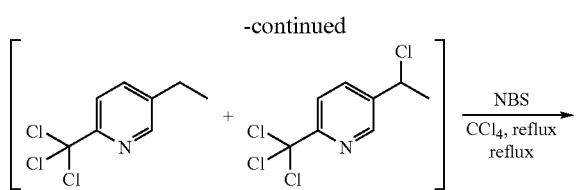

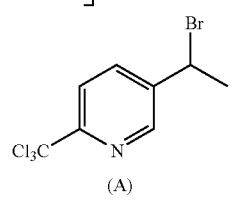

A mixture of 5-ethylpyridine-2-carboxylic acid (1.98 g, 13 mmol), phenyl-phosphonic dichloride (2.8 g, 14.3 mmol), phosphorus pentachloride (7.7 g, 32 mmol) was stirred and slowly heated. Once a clear yellow liquid was formed, the mixture was heated to reflux overnight. After cooling, the volatiles were removed under reduced pressure. The residue was carefully poured into saturated sodium carbonate aqueous solution cooled in an ice-water bath. The aqueous phase was then extracted with $CH_2Cl_2$ twice. The combined organic layer was washed with brine, dried over anhydrous $Na_2SO_4$, filtered, concentrated, and partially purified on silica gel eluted with 10% EtOAc in hexane (v/v) to give 2.7 g of crude product containing both 5-ethyl-2-(trichloromethyl)pyridine and 5-(1-chloroethyl)-2-(trichloromethyl)pyridine in an approximate 3:1 ratio (GC data, masses calcd for $C_8H_8Cl_3N$ and $C_8H_7Cl_4N$ $[M]^+$ 223 and 257 respectively. Found 223 and 257 respectively).

A mixture of the above-mentioned crude product (2.6 g) in carbon tetrachloride (100 mL) was treated with ca 80% of N-bromosuccinimide (1.9 g, 11 mmol) and benzoylperoxide (0.66 g, 0.275 mmol) and refluxed overnight. The solid was filtered off, the filtrate concentrated and the resulting residue purified on silica gel using 4% EtOAc in hexane (v/v) to give 1.0 g of the desired product 5-(1-bromoethyl)-2-(trichloromethyl)pyridine (A) as a yellow solid. The combined yield for the two steps was 25%. GC-MS: mass calcd for $C_8H_7BrCl_3N$ $[M-1-Cl]^+$ 266. Found 266.

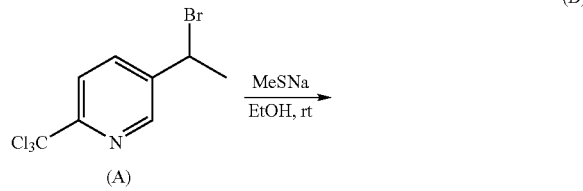

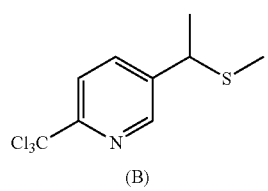

A solution of 5-(1-bromoethyl)-2-(trichloromethyl)pyridine (A) (0.95 g, 3.14 mmol) in ethanol (15 mL) was treated with sodium thiomethoxide (0.44 g, 6.29 mmol) portionwise at 0° C. The mixture was stirred at room temperature overnight. The solvent ethanol was then removed under a reduced pressure and the residue was re-taken into $CH_2Cl_2$ and brine. The two phases were separated and the organic layer was dried over anhydrous $Na_2SO_4$, filtered and concentrated. The residue was purified on silica gel using 5% EtOAc in hexane v/v to give 0.57 g of the partially pure 5-[1-(methylthio) ethyl]-2-(trichloromethyl)pyridine (B) in 67% crude yield. GC-MS: mass calcd for $C_9H_{10}Cl_3NS$ $[M]^+$ 269. Found 269.

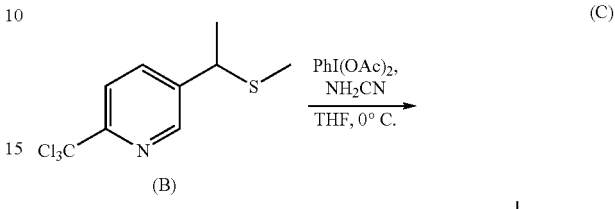

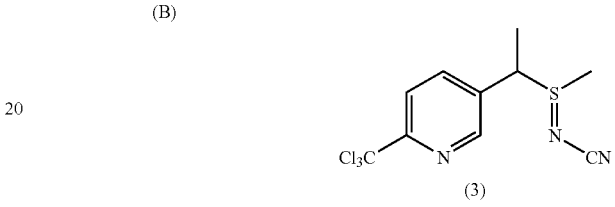

To a stirred solution of 5-[1-(methylthio)ethyl]-2-(trichloromethyl)-pyridine (B) (0.55 g, 2.3 mmol) and cyanamide (0.097 g, 2.3 mmol) in THF (7 mL) cooled to 0° C. was added iodobenzene diacetate (0.75 g, 2.3 mmol) in one portion. The resulting mixture was stirred at 0° C. for 1 hr and then at room temperature for 2 hr. The solvent was removed in vacuo and the resulting mixture was purified on silica gel using 50% acetone in hexane (v/v) to give 0.254 g of {1-[6-(trichloromethyl)pyridin-3-yl]ethyl}(methyl)-$\lambda^4$-sulfanylidenecyanamide (3) as an off-white solid in 40% yield. $^1$H NMR for the diastereomeric mixture (300 MHz, $d_6$-acetone) δ 8.87 (s, 1H), 8.21-8.25 (m, 2H), 4.65-4.76 (m, 1H), 2.86-2.66 (m, 3H), 1.88-1.92 (m, 3H).

Example IV

Preparation of (1E)-[1-(2-chloropyrimidin-5-yl) ethyl](methyl)-$\lambda^4$-sulfanylidenecyanamide (4)

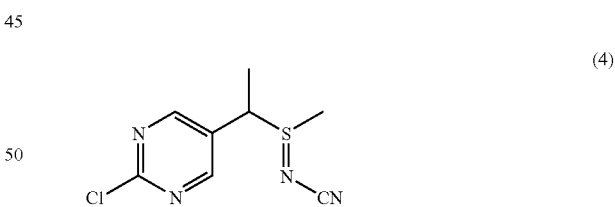

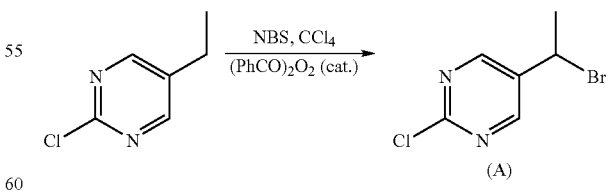

A solution of 2-chloro-5-ethylpyrimidine (1.15 g, 8.1 mmol) in 20 mL of carbon tetrachloride was treated with N-bromosuccinimide (1.50 g, 8.4 mmol) and a catalytic amount of benzoyl peroxide and the mixture heated to 75° C. After several hours and additional catalyst, the starting material was completely consumed. The solid was removed and the filtrate concentrated under reduced pressure. The resulting residue was purified by flash column chromatography on silica gel using a mixture of ethyl acetate and petroleum ether as the eluting solvent. The solvents were removed under reduced pressure to yield 0.64 g (36%) of 5-(1-bromoethyl)-2-chloropyrimidine (A) as a clear liquid: $^1$H NMR (CDCl$_3$) δ 8.70 (s, 2H), 5.15 (q, J=8.0 Hz, 1H), 2.10 (d, J=8.0 Hz, 3H); GCMS (FID) m/z 222 (M+). Some of the corresponding dibromo compound 0.44 g (18%) was also isolated, as a white solid: mp 84-85° C.; $^1$H NMR (CDCl$_3$) d 9.00 (s, 2H), 3.00 (s, 3H); LCMS (ESI) m/z 298 (M+H).

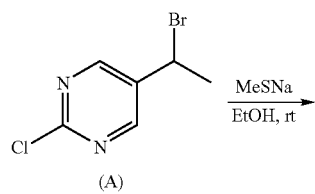

2-Chloro-5-[1-(methylthio)ethyl]pyrimidine (B) was obtained as a pale yellow syrup from bromide (A) using the same procedure described in Example III (B) above. $^1$H NMR (CDCl$_3$) δ 8.60 (s, 2H), 3.85 (q, J=8.0 Hz, 1H), 1.98 (s, 3H), 1.65 (d, J=8.0 Hz, 3H); GCMS (FID) m/z 188 (M+).

Title compound (1E)-[1-(2-chloropyrimidin-5-yl)ethyl](methyl)-λ$^4$-sulfanylidenecyanamide (4) was obtained as a pale orange syrup and a 2:1 mixture of diastereomers from sulfide (B) using the same procedure described in Example III (C) above. Major diastereomer: $^1$H NMR (CDCl$_3$) δ 8.68 (s, 2H), 4.38 q, J=8.3 Hz, 1H), 2.68 (s, 3H), 1.92 (d, J=8.3 Hz, 3H); LC-MS (ESI) m/z 229 (M+H).

Example V

Preparation of (1E)-methyl{[2-(trifluoromethyl)-1,3-thiazol-5-yl]methyl}-λ$^4$-sulfanylidenecyanamide (5)

5-[(methylthio)methyl]-2-(trifluoromethyl)-1,3-thiazole (B) was obtained as a pale orange liquid from 5-(bromomethyl)-2-(trifluoromethyl)-1,3-thiazole (A) [U.S. Pat. No. 5,338,856] using the same procedure described in Example III (B). $^1$H NMR (CDCl$_3$) δ 7.75 (s, 1H), 3.90 (s, 2H), 2.10 (s, 3H); GC-MS (FID) m/z 213 (M+).

(1E)-methyl{[2-(trifluoromethyl)-1,3-thiazol-5-yl]methyl}-λ$^4$-sulfanyl-idenecyanamide was obtained as a pale yellow syrup from sulfide (B) using the same procedure described in Example III (C) above.: $^1$H NMR (CDCl$_3$) δ 8.00 (s, 1H), 4.60 (s, 2H), 2.85 (s, 3H); LCMS (ESI) m/z 254 (M+H).

Example VI

Preparation of 3-[6-(trifluoromethyl)pyridin-3-yl]tetrahydro-1H-1λ$^4$-thien-1-ylidenecyanamide (6)

Tetrahydrothien-3-one (9.947 g, 97.37 mmol) was placed in a 250 mL Parr bomb. Triphenylphosphine (28.09 g, 108.0 mmol) was added followed by $CH_3I$ (0.30 mL, 4.8 mmol) and dimethyl carbonate (10.0 mL, 119 mmol). The reactor was purged with nitrogen and then heated for 3 hr at 175° C. The reaction mixture was cooled to room temperature and purified by Kugelrohr distillation to give 3-methylene-tetrahydrothiophene as a colorless liquid (7.65 g) which contained the desired olefin along with methanol and benzene. The desired olefin was used without further purification. $^1$H NMR ($CDCl_3$) δ 4.77 (m, 1H, olefinic H), 4.72 (m, 1H, olefinic H), 2.63 (t, J=7 Hz, 2H, H5), 2.55 (s, 2H, H2), 2.41 (br t, J=7 Hz, 2H, H4). $^{13}C\{^1H\}$ NMR ($CDCl_3$) δ 107.3 (olefinic $CH_2$), 36.7, 35.2, 30.4. GC-MS (EI): 100 [m]$^+$.

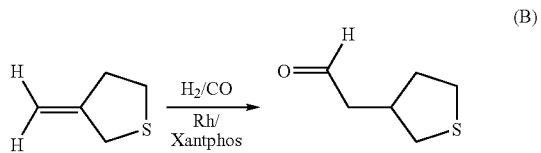

(B)

3-Methylene-tetrahydrothiophene (5.88 g, as mixture with benzene and methanol) was placed in a 25 mL Parr bomb which contained a magnetic stir bar. $Rh(CO)_2(acac)$ (149 mg, 0.58 mmol) and 4,5-bis(diphenylphosphino)-9,9-dimethylxanthene (Xantphos) (355 mg, 0.61 mmol) were added as solids. The reactor was sealed and purged with CO before pressurizing to 350 psi. Hydrogen was then added to bring the total pressure to 700 psi. The reactor was heated to 80° C. with magnetic stirring for 14 h. The reaction mixture was cooled to room temperature. GC-MS indicated the presence of a single aldehyde regioisomer along with benzene and methanol. No starting olefin was evident. Solvent was removed under vacuum and the product (tetrahydrothien-3-yl acetaldehyde) was isolated by Kugelrohr distillation (50° C./0.01 mm) as a colorless liquid (1.1 g). $^1$H NMR (acetone-$d_6$) δ 9.76 (t, J=1.4 Hz, 1H, $CH_2CHO$), 2.97 (m, 1H), 2.83 (d, J=5.7 Hz, 1H), 2.80 (d, J=5.4 Hz, 1H), 2.62 (br s, 3H), 2.46 (m, 1H), 2.17 (m, 1H), 1.61 (m, 1H). GC-MS (EI): 130 [m]$^+$.

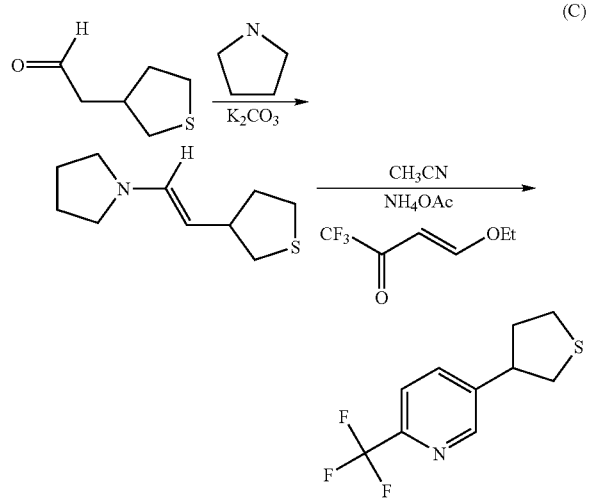

(C)

Neat tetrahydrothien-3-yl acetaldehyde (1.10 g, 8.45 mmol) was placed in a vial which was purged with nitrogen. The vial was cooled in an ice bath, and solid $K_2CO_3$ (0.584 g, 4.23 mmol) was added. Neat pyrrolidine (1.70 mL) was added dropwise over 5 min. The ice bath was removed, and the reaction mixture was stirred under $N_2$ for 20 h. GC-MS showed clean formation of the desired enamine. The solid was washed with four 10 mL portions of ether. The combined ether extracts were evaporated under vacuum to give the intermediate enamine as a light yellow oil (1.617 g). 3-Ethoxy-1-trifluoromethylpropenal (1.634 g, 9.72 mmol) was dissolved in anhydrous $CH_3CN$ (5 mL) under nitrogen. The solution was cooled in an ice bath. A solution of enamine (1.617 g) in 2 mL $CH_3CN$ was added dropwise over 10 min. The ice bath was removed and solution allowed to warm to room temperature and continue to stir over 2 h. Ammonium acetate (1.407 g, 18.25 mmol) was added and the reaction mixture was refluxed under nitrogen for 1 h. The solution was cooled to room temperature and $CH_3CN$ was evaporated under vacuum. The resulting red oil was purified by column chromatography on silica with hexane-ethyl acetate to yield 5-tetrahydrothien-3-yl-2-(trifluoromethyl)pyridine (1.08 g; 52.3% yield) as an orange crystalline solid. $^1$H NMR ($CDCl_3$) δ 8.68 (d, J=1.6 Hz, 1H, pyridine H6), 7.83 (dd, J=1.6, 8.0 Hz, 1H, pyridine H4), 7.65 (d, J=8.0 Hz, 1H, pyridine H3), 3.48 (m, 1H), 3.24 (dd, J=6.8, 10 Hz, 1H), 3.09-2.90 (m, 3H), 2.47 (m, 1H), 2.11 (m, 1H). GC-MS (EI): 233 [m]$^+$.

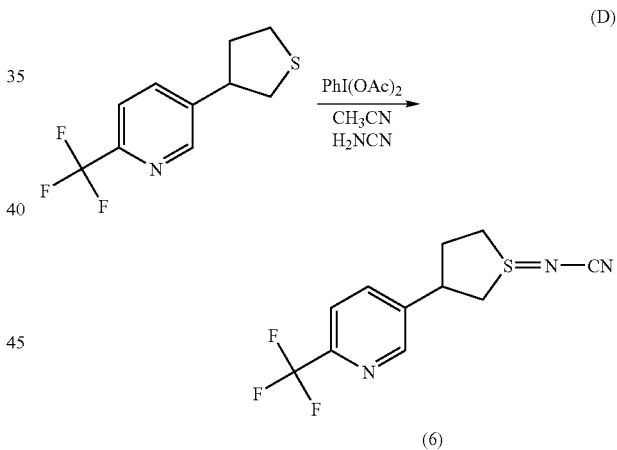

(D)

(1E)-3-[6-(trifluoromethyl)pyridin-3-yl]tetrahydro-1H-1λ$^4$-thien-1-ylidenecyanamide (6) was obtained from 5-(tetrahydrothien-3-yl)-2-trifluoro-methylpyridine as an off-white powder using the same procedure described in Example III (C) above. The $^1$H NMR spectrum of this solid exhibited resonances for a 1:1 mixture of diastereomers. $^1$H NMR (acetone-$d_6$) δ 8.85 (d, J=2.2 Hz, 1H, pyridine H6), 8.83 (d, J=2.2 Hz, 1H, pyridine H6), 8.26 (dd, J=2.2, 8.3 Hz, 1H, pyridine H4), 8.15 (dd, J=2.2, 8.3 Hz, 1H, pyridine H4), 7.90 (d, J=8.3 Hz, 1H, pyridine H3), 7.86 (d, J=8.3 Hz, 1H, pyridine H3), 4.38 (dd, J=8.7, 14 Hz, 1H), 4.23 (tt, J=6, 12 Hz, 1H), 4.16 (ddd, J=2.6, 8.3, 11.2 Hz, 1H), 3.83 (td, J=8.7, 18 Hz, 1H), 3.68-3.48 (m, 3H), 3.29-3.17 (m, 2H), 2.95 (m, 1H), 2.85-2.79 (m, 3H), 2.33 (m, 1H). LC-MS (ELSD): 273 [m]$^+$.

Example VII

Preparation of [(5-fluoro-6-chloropyridin-3-yl)methyl](methyl)-λ⁴-sulfanylidenecyanamide (7)

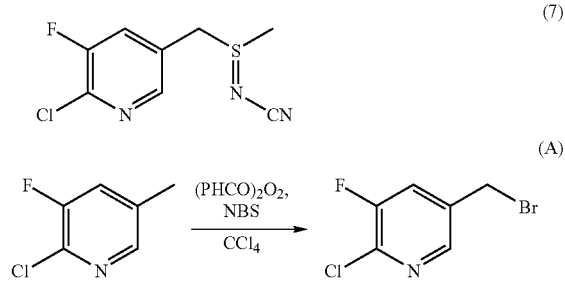

(7)

(A)

A suspension of 2-chloro-3-fluoro-5-methylpyridine (5.1 g, 35 mmol), N-bromosuccinimide (6.1 g, 35 mmol) and benzolyperoxide (0.16 g, 0.66 mmol) in carbon tetrachloride (100 mL) was refluxed overnight. Upon cooling down, the solid was filtered off and the filtrate was concentrated and loaded onto a silica gel column eluted with 5% EtOAc in hexane to give 3.77 g of the desired 2-chloro-3-fluoro-5-bromomethylpyridine as colorless oil in 48% yield. GC-MS calcd. for $C_6H_4BrClFN$: 224.46. Found: 224.

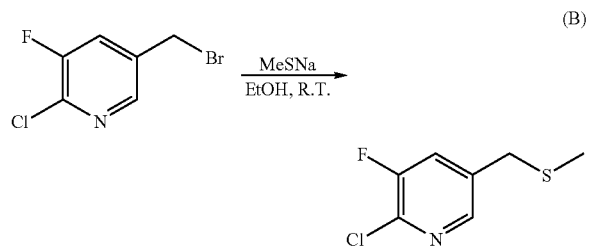

(B)

2-chloro-3-fluoro-5-methylthiomethylpyridine was obtained from 2-chloro-3-fluoro-5-bromomethylpyridine using the same procedure described in Example III (B) above. GC-MS calcd. for $C_7H_7ClFNS$: 191.66. Found: 191.

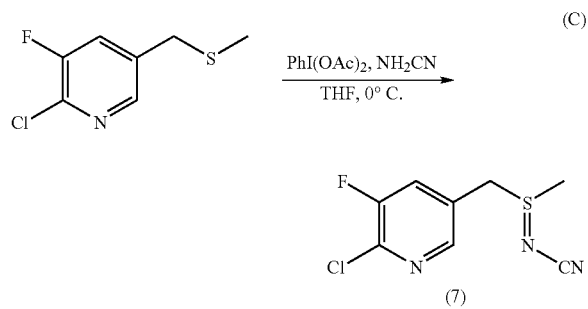

(C)

[(5-fluoro-6-chloropyridin-3-yl)methyl]methyl-λ⁴-sulfanylidenecyanamide (7) was obtained as an off-white solid from 2-chloro-3-fluoro-5-methylthio-methylpyridine using the same procedure described in Example III (C). LC-MS calcd. for $C_8H_7ClFN_3S$ [M+1]⁺: 232.69. Found: 232.04.

Example VIII

Preparation of [(6-(1,1-difluoroethylpyridin-3-yl)methyl](methyl)-λ⁴-sulfanylidenecyanamide (8)

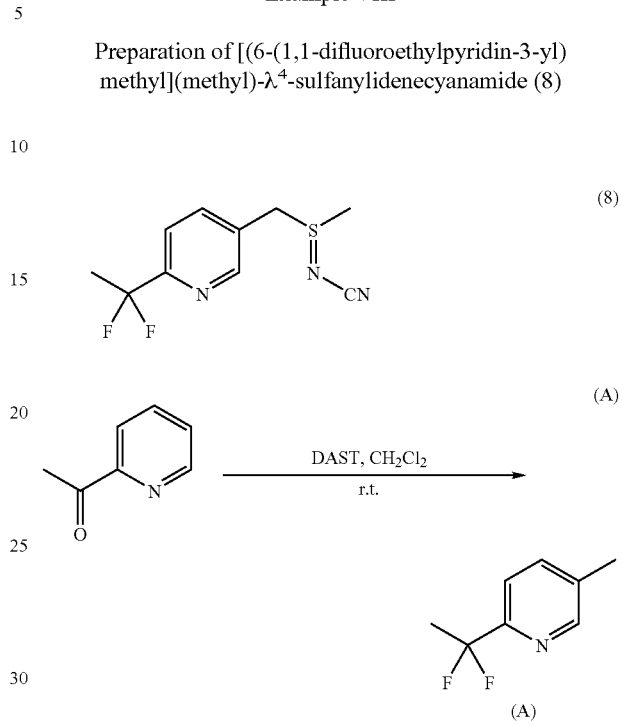

(8)

(A)

To a solution 5-methyl-2-acetylpyridine (9.9 g, 73.3 mmol) in molecule sieves-dried $CH_2Cl_2$ (150 mL) was added diethylamino sulfur trifluoride (DAST) (25.8 g, 260 mmol) at room temperature and the mixture was stirred at room temperature overnight. More DAST (12 g, 74 mmol) was added and the reaction continued for two more days after which an additional DAST (3.8 g, 23 mmol) was added and the reaction continued for another 3 days. After the reaction was quenched slowly with saturated $NaHCO_3$ at 0° C., the organic phase was separated, dried over $Na_2SO_4$, filtered, and concentrated. The residue was purified on silica gel eluted with 8% EtOAc in hexane (v/v) to give 3.91 g of 2-(1,1-difluoroethyl)-5-methylpyridine (A) as a light brownish oil in 34% yield. GC-MS: mass calcd for $C_8H_9F_2N$ [M]⁺ 157. Found 157.

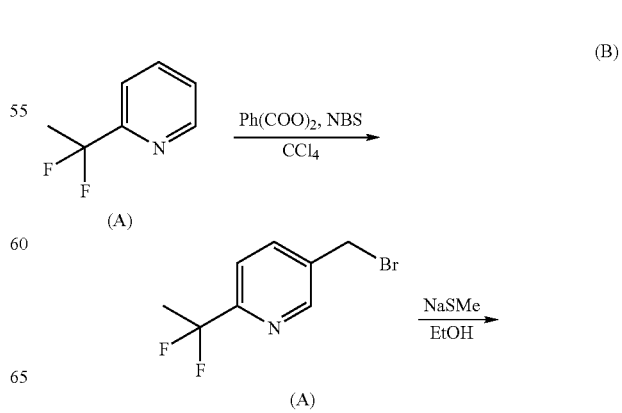

(B)

(A)

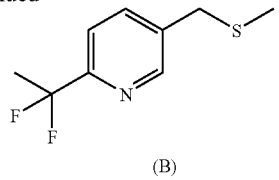

(B)

A mixture of 2-(1,1-difluoroethyl)-5-methylpyridine (A) (2.0 g, 12.7 mmol), N-bromosuccinimide (2.2 g, 12.7 mmol) and benzoylperoxide (0.15 g, 0.63 mmol) in carbon tetrachloride (100 mL) was refluxed overnight. After the solid was removed by filtration, the filtrate was concentrated. The residue was re-dissolved in ethanol (40 mL) and sodium thiomethoxide (1.33 g, 19 mmol) was added at room temperature and stirred for 3 h. The solvent was removed under reduced pressure and the remaining mixture was dissolved in $CH_2Cl_2$ and water. After separation, the organic layer was dried over $Na_2SO_4$, filtered and concentrated. The crude product 2-(1,1-difluoroethyl)-5-methylthiomethylpyridine (B) was 94% pure on GC/MS, which was used directly for the next reaction without further purification. GC-MS: mass calcd for $C_9H_{11}F_2NS$ [M]+ 203. Found 203.

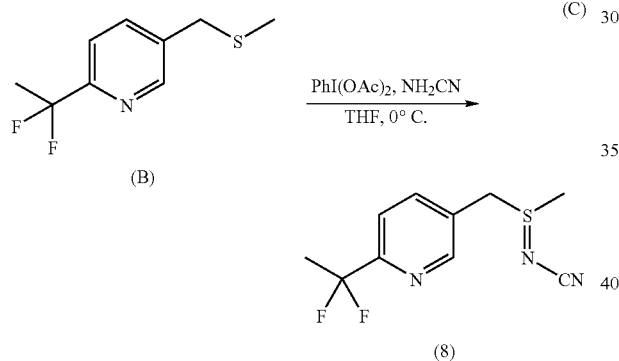

[(6-(1,1-difluoroethylpyridin-3-yl)methyl](methyl)-$\lambda^4$-sulfanylidenecyanamide (8) was obtained from 2-(1,1-difluoroethyl)-5-methylthiolmethylpyridine (B) as a brownish solid using the same procedure described in Example III (C). LC-MS: mass calcd for $C_{10}H_{11}F_2N_3S$ [M]+ 243.28. Found [M+1]+ 244.11.

Example IX

Preparation of_cis-[2-(6-chloropyridin-3-yl)cyclopentyl](methyl)-$\lambda^4$-sulfanylidenecyanamide (9)

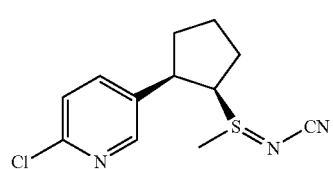

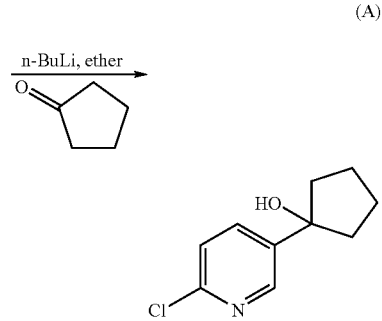

5-Bromo-2-chloropyridine (3.0 g, 15.6 mmol) was dissolved in diethyl ether (100 mL) in an oven-dried, nitrogen-flushed 250 mL round bottom flask and cooled in a dry ice/acetone bath under nitrogen. n-BuLi (1.05 g, 16.4 mmol, 6.6 mL of a 2.5 M solution in hexanes) was added via syringe and the and the orange heterogenous mixture allowed to stir for 1 hour. Cyclopentanone (1.3 g, 15.6 mmol) was added via syringe and the mixture allowed to warm to −20° C. before being quenched with 1N HCl. The mixture was extracted with EtOAc and the organic extract washed with sat. $NaHCO_3$. The $NaHCO_3$ wash was used to neutralize the first aqueous layer and the combined aqueous layers were extracted with additional EtOAc and the combined organic layers dried ($Na_2SO_4$), filtered, concentrated, and purified by flash silica gel chromatography (hexanes:EtOAc; 2:1) to give 1-(6-chloropyridin-3-yl)cyclopentanol (2.33 g, 76%) as an off-white solid: mp 92-93° C., LC/MS (ESI) m/z 197, $^1$H NMR (300 MHz, $CDCl_3$) δ 8.50 (d, 1H, J=2.4 Hz), 7.77 (dd, 1H, J=8.4, 2.4 Hz), 7.28 (d, 1H, J=8.4 Hz), 2.05-1.80 (m, 8H), 1.60 (s, 1H, OH).

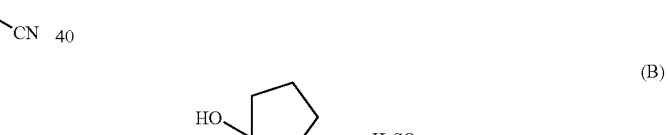

1-(6-Chloropyridin-3-yl)cyclopentanol (2.1 g, 10.5 mmol) was treated with acetic acid (12 mL) and sulfuric acid (4 mL) and the mixture heated to reflux for 30 min. After cooling to room temperature, ice and 2 N NaOH (180 mL) was add and the resulting tan precipitate collected by filtration, washed with $H_2O$ and dried giving 2-chloro-5-(cyclopent-1-enyl)pyridine (1.66 g, 88%) as a tan solid: mp 59-60° C., LC/MS (ESI) m/z 179, $^1$H NMR (300 MHz, $CDCl_3$) δ 8.41 (d, 1H, J=2.4 Hz), 7.66 (dd, 1H, J=8.4, 2.4 Hz), 7.25 (d, 1H, J=8.4 Hz), 6.27 (t, 1H, J=2.1 Hz), 2.69 (bm, 2H), 2.55 (bm, 2H), 2.05 (m, 2H).

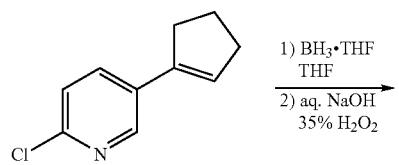

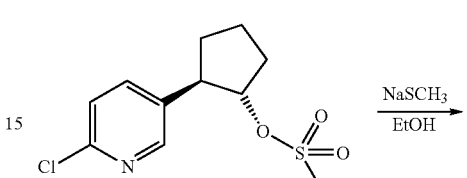

2-Chloro-5-(cyclopent-1-enyl)pyridine (1.5 g, 8.5 mmol) was dissolved in THF (30 mL) in an oven-dried, nitrogen-flushed 250 mL round bottom flask and the resulting solution cooled in a dry ice/acetone bath under nitrogen. BH$_3$.THF complex (2.4 g, 28.0 mmol, 28 mL of a 1 M solution in THF) was added dropwise with stirring via syringe and the mixture was allowed to warm slowly to room temperature and stir overnight. 2 N NaOH (15 mL), ethanol (15 mL) and 35% H$_2$O$_2$ (10 mL) were added and the mixture stirred for 0.5 h and then diluted with EtOAc and 1 N HCl. The layers were separated and the organic layer washed with brine and aqueous NaHSO$_3$, dried over Na$_2$SO$_4$, filtered through celite, and concentrated. Purification by flash chromatography (hexanes:EtOAc/10:1→2:1) gave in order of elution by-products 2-chloro-5-cyclopentylpyridine (0.45 g, 29%) and 1-(6-chloropyridin-3-yl)cyclopentanol (0.44 g, 26%) followed by the desired product trans-2-(6-chloropyridin-3-yl)cyclopentanol (0.25 g, 15%) as a clear oil: LC/MS (ESI) m/z 197, $^1$H NMR (300 MHz, CDCl$_3$) δ 8.26 (d, 1H, J=2.4 Hz), 7.55 (dd, 1H, J=8.4, 2.4 Hz), 7.25 (d, 1H, J=8.4 Hz), 4.12 (m, 1H), 2.88 (m, 1H), 2.24-1.62 (m, 6H).

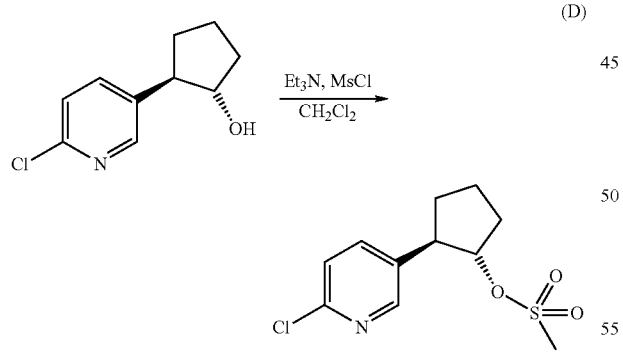

trans-2-(6-Chloropyridin-3-yl)cyclopentanol (0.225 g, 1.14 mmol) was dissolved in CH$_2$Cl$_2$ (10 mL) in a 50 mL round bottomed flask, the solution cooled in an ice bath under nitrogen and treated with Et$_3$N (0.172 g, 1.71 mmol, 0.24 mL) and methanesulfonyl chloride (0.163 g, 1.42 mmol, 0.11 ml) via syringe with stirring. After 1 h, TLC (hexanes:EtOAc/2:1) indicated complete conversion. The reaction mixture was concentrated in vacuo and then partitioned between EtOAc and 1 N HCl. The layers were separated and the organics was dried (Na$_2$SO$_4$), filtered and concentrated to give trans-methanesulfonic acid 2-(6-chloropyridin-3-yl)cyclopentyl ester (0.303 g, 97%) as an oil: LC/MS (ESI) m/z 275, $^1$H NMR (300 MHz, CDCl$_3$) δ 8.28 (d, 1H, J=2.7 Hz), 7.56 (dd, 1H, J=8.1, 2.7 Hz), 7.3 (d, 1H, J=8.1 Hz), 4.93 (apparent q, 1H, J=5.7 Hz), 3.28 (apparent q, 1H, J=8.7 Hz), 2.86 (s, 3H), 2.26 (m, 2H), 2.10-1.80 (m, 3H), 1.73 (m, 1H).

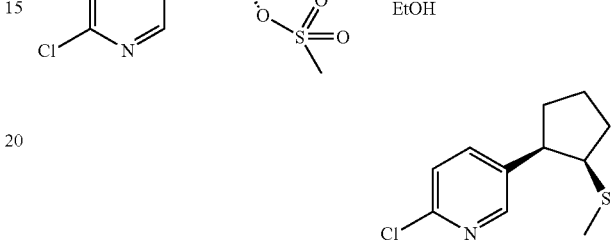

trans-Methanesulfonic acid 2-(6-chloropyridin-3-yl)cyclopentyl ester (0.295 g, 1.07 mmol) was dissolved in EtOH (5 mL) in a 25 mL round bottom flask and cooled in an ice bath under nitrogen. Sodium methane thiolate (0.224 g, 3.20 mmol) was added all at once at the cloudy white mixture was allowed to warm to room temperature and stir overnight. The mixture was diluted with EtOAc and brine and the layers were separated. The organic layer was washed with brine, dried (Na$_2$SO$_4$), filtered, and concentrated. Purification by flash silica gel chromatography (hexanes:EtOAc/10:1) gave cis-2-chloro-5-(2-methylthio-cyclopentyl)pyridine (0.148 g, 61%) as an oil: LC/MS (ESI) m/z 227, $^1$H NMR (300 MHz, CDCl$_3$) δ 8.27 (d, 1H, J=2.7 Hz), 7.60 (dd, 1H, J=8.1, 2.7 Hz), 7.26 (d, 1H, J=8.1 Hz), 3.30 (m, 2H), 2.24 (m, 1H), 2.15-1.65 (m, 5H), 1.74 (s, 3H).

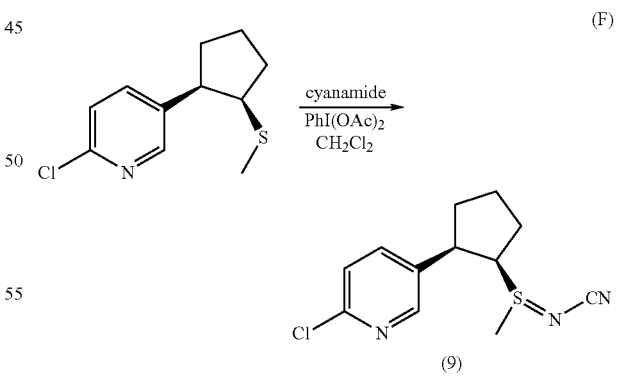

cis-[2-(6-Chloropyridin-3-yl)cyclopentyl](methyl)-λ$^4$-sulfanylidene-cyanamide (9) was obtained as an oily 1:1 mixture of diastereomers from cis-2-chloro-5-(2-methylthiocyclopentyl)pyridine using the same procedure described in Example III (C). LC/MS (ESI) m/z 267, $^1$H NMR (300 MHz, CDCl$_3$) δ 8.31 (d, 2H, J=2.7 Hz), 7.70 (dd, 1H, J=8.4, 2.7 Hz), 7.63 (dd, 1H, J=8.4, 2.7 Hz), 7.40 (d, 1H, J=8.4 Hz), 7.32 (d, 1H, J=8.4 Hz), 3.96 (m, 1H), 3.81 (m, 1H), 3.67-3.51 (m, 2H), 2.73 (s, 3H), 2.59 (m, 1H), 2.45 (s, 3H), 2.40-1.95 (m, 9H), 1.85 (m, 2H).

Example X

Preparation of [(4,6-dichloropyridin-3-yl)methyl](methyl)-λ⁴-sulfanylidenecyanamide (10)

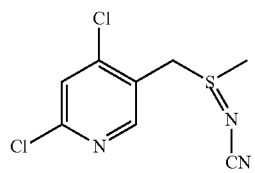

(10)

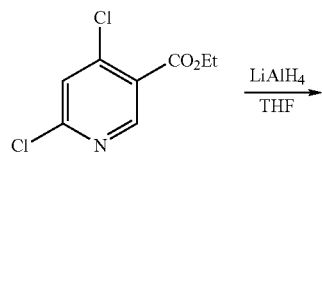

(A)

To a stirred solution of ethyl 4,6-dichloronicotinate (8.8 g, 40 mmol) in anhydrous THF (75 mL) cooled in an ice-water bath was added in a dropwise fashion 1 M LiAlH₄ solution in THF (25 mL, 25 mmol). During the addition, the temperature was not allowed to rise above 25° C. After the addition was over, the reaction was warmed to 40° C. for 15 min, cooled, then quenched by the successive dropwise addition of water (0.95 mL), 15% aqueous NaOH (0.95 mL) and water (1.85 mL). The mixture was filtered through celite and the filtrated was dried (MgSO₄), passed through a short pad of silica gel and concentrated to give a red oil. Ether (100 mL) was added whereupon a gummy precipitate immediately appeared which was removed by filtration. The ether solution was allowed to stand at room temperature overnight, during which time more precipitate was formed which was removed again by filtration. The ether solution was concentrated and dried to give 3.25 g of the product 2,4-dichloro-5-hydroxy-methylpyridine in 46% yield as a nearly colorless oily solid. ¹H NMR (300 MHz, CDCl₃) δ 8.5 (s, 1H), 7.4 (s, 1H), 4.8 (s, 2H), 2.7 (bs, 1H); GC-MS: mass calcd for $C_6H_5Cl_2NO$ [M]⁺, 177. Found 177.

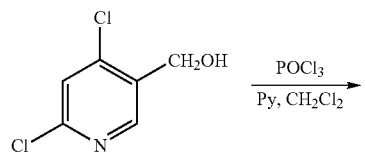

(B)

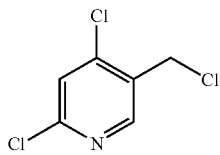

The starting material 2,4-dichloro-5-hydroxymethylpyridine (3.2 g, 18 mmol) was converted into 2.0 g of 2,4-dichloro-5-chloromethylpyridine (57% yield) as a yellow oil using the same procedure as describe in Example II (D). ¹H NMR (300 MHz, CDCl₃) δ 8.4 (s, 1H), 7.4 (s, 1H), 4.7 (s, 2H); GC-MS: mass calcd for $C_6H_4Cl_3N$ [M]⁺, 195. Found 195.

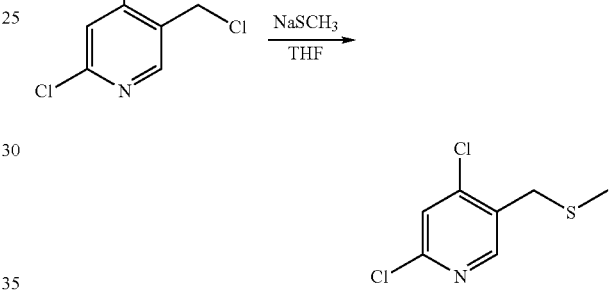

(C)

2,4-Dichloro-5-methylthiomethylpyridine (2.0 g, 94% yield) was prepared as a yellow oil from 2,4-dichloro-5-chloromethylpyridine (2.0 g, 1.0 mmol) by using the same method as described in Example I, procedure A. ¹H NMR (300 MHz, CDCl₃) δ 8.3 (s, 1H), 7.4 (s, 1H), 3.7 (s, 2H), 2.0 (s, 3H); GC-MS: mass calcd for $C_7H_7Cl_2NS$ [M]⁺, 207. Found 207.

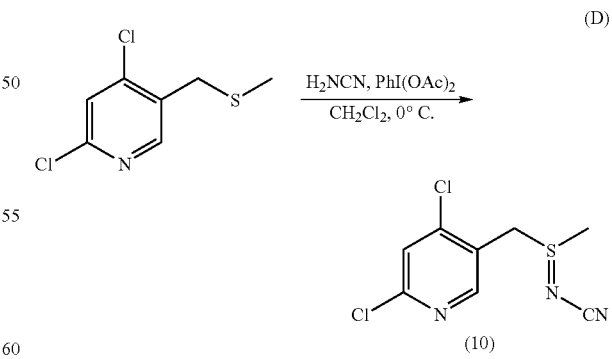

(D)

[(4,6-Dichloropyridin-3-yl)methyl](methyl)-λ⁴-sulfanylidene-cyanamide (10) was prepared as a pale yellow gum from 2,4-dichloro-5-methylthiomethylpyridine using the same method as described in Example I (B). ¹H NMR (400 MHz, DMSO) δ 8.48 (s, 1H), 7.93 (s, 1H), 4.68 (d, 1H), 4.49

(d, 1H), 2.95 (s, 3H); LC-MS (ELSD): mass calcd for $C_8H_7Cl_2N_3S$ [M]$^+$ 248. Found 248.

Example XI

Insecticidal Testing

The compounds identified in the foregoing examples were tested against cotton aphid and green peach aphid using procedures described hereinafter.

Insecticidal Test for Cotton Aphid (*Aphis Gossypii*) in Foliar Spray Assay

Squash with fully expanded cotyledon leaves were trimmed to one cotyledon per plant and infested with cotton aphid (wingless adult and nymph) 1 day prior to chemical application. Each plant was examined before chemical application to ensure proper infestation (ca. 30-70 aphids per plant). Compounds (2 mg) were dissolved in 2 ml of acetone: methanol (1:1) solvent, forming stock solutions of 1000 ppm. The stock solutions were diluted 5× with 0.025% Tween 20 in $H_2O$ to obtain a solution at 200 ppm. Lower concentrations (50, 12.5 and 3.13 ppm) were prepared by making sequential 4× dilutions from the 200 ppm solution with a diluent consisting 80 parts of 0.025% Tween 20 in $H_2O$ and 20 parts of acetone:methanol (1:1). A hand-held Devilbiss sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for 3 days at approximately 23° C. and 40% RH before the number of live aphids on each plant was recorded. Insecticidal activity was measured by Corrected % Control using Abbott's correction formula and presented in Table 1:

Corrected % Control=100*(X−Y)/X where X=No. of live aphids on solvent check plants
Y=No. of live aphids on treated plants Insecticidal Test for Green Peach Aphid (*Myzus Persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 2-3 days prior to chemical application. Four seedlings were used for each treatment. Compounds (2 mg) were dissolved in 2 ml of acetone:methanol (1:1) solvent, forming stock solutions of 1000 ppm. The stock solutions were diluted 5× with 0.025% Tween 20 in $H_2O$ to obtain a solution at 200 ppm. Lower concentrations (50, 12.5 and 3.13 ppm) were prepared by making sequential 4× dilutions from the 200 ppm solution with a diluent consisting 80 parts of 0.025% Tween 20 in $H_2O$ and 20 parts of acetone:methanol (1:1). A hand-held Devilbiss sprayer was used for spraying a solution to both sides of cabbage leaves until runoff. Reference plants (solvent check) were sprayed with the diluent only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where X=No. of live aphids on solvent check plants
Y=No. of live aphids on treated plants The Corrected % Control values from assays are given in Table 1.

TABLE 1

| Comp # | CA 200 | CA 50 | GPA 200 | GPA 50 |
|--------|--------|-------|---------|--------|
| 1 | A | D | G | G |
| 2 | A | A | A | A |
| 3 | A | A | A | A |
| 4 | A | C | F | G |
| 5 | A | E | G | G |
| 6 | A | A | C | E |
| 7 | A | A | C | D |
| 8 | A | A | A | D |
| 9 | D | G | D | G |
| 10 | B | G | G | G |

CA 200 refers to % control at 200 ppm against cotton aphid in foliar spray tests,
CA 50 refers to % control at 50 ppm against cotton aphid in foliar spray tests,
GPA 200 refers to % control at 200 ppm against green peach aphid in foliar spray tests,
GPA 50 refers to % control at 50 ppm against green peach aphid in foliar spray tests.

In each case of Table 1 the rating scale is as follows:

| % Control (or Mortality) | Rating |
|--------------------------|--------|
| 90-100 | A |
| 80-89 | B |
| 70-79 | C |
| 60-69 | D |
| 50-59 | E |
| Less than 50 | F |
| Inactive | G |
| Not tested | H |

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophiuim dirhoduim*, *Schizaphis graminum*, *Brachycolus noxius*, *Nephotettix* spp., *Nilaparvata lugens*, *Sogatellafurcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*, *Cimex lectularius*, *Cimex hemipterus*

Thysanoptera—*Frankliniella* spp., *Thrips* spp., *Scirtothrips dorsalis*

Isoptera—*Reticulitermes flavipes*, *Coptotermes formosanus*, *Reticulitermes virginicus*, *Heterotermes aureus*, *Reticulitermes hesperus*, *Coptotermes frenchii*, *Shedorhinotermes* spp., *Reticulitermes santonensis*, *Reticulitermes grassei*, *Reticulitermes banyulensis*, *Reticulitermes speratus*, *Reticulitermes hageni*, *Reticulitermes tibialis*, *Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica*, *Aedes* spp., *Culex* spp., *Anopheles* spp., *Fannia* spp., *Stomoxys* spp., Hymenoptera—*Iridomyrmex humilis*, *Solenopsis* spp., *Monomorium pharaonis*, *Atta* spp., *Pogonomyrmex* spp., *Camponotus* spp., *Monomorium* spp., *Tapinoma sessile*, *Tetramorium* spp., *Xylocapa* spp., *Vespula* spp., *Polistes* spp.

Mallophaga (chewing lice)

Anoplura (sucking lice)—*Pthirus pubis*, *Pediculus* spp.

Orthoptera (grasshoppers, crickets)—*Melanoplus* spp., *Locusta migratoria*, *Schistocerca gregaria*, *Gryllotalpidae* (mole crickets).

Blattoidea (cockroaches)—*Blatta orientalis*, *Blattella germanica*, *Periplaneta americana*, *Sipella longipalpa*, *Periplaneta australasiae*, *Periplaneta brunnea*, *Parcoblatta pennsylvanica*, *Periplaneta fuliginosa*, *Pycnoscelus surinamensis*, Siphonaptera—*Ctenophalides* spp., *Pulex irritans*

Acari—*Tetranychus* spp., *Panonychus* spp., *Eotetranychus carpini*, *Phyllocoptruta oleivora*, *Aculus pelekassi*, *Brevipalpus phoenicis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Nematoda—*Dirofilaria immitis*, *Meloidogyne* spp., *Heterodera* spp., *Hoplolaimus columbus*, *Belonolaimus* spp., *Pratylenchus* spp., *Rotylenchus reniformis*, *Criconemella ornata*, *Ditylenchus* spp., *Aphelenchoides besseyi*, *Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus,* and *X. bovienii,* plant incorporated protectant insecticides such as Cry1Ab, Cry1Ac, Cry1F, Cry1A.105, Cry2Ab2, Cry3A, mir Cry3A, Cry3B1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid; imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, suiprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite;

benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluorornidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:

1. Compounds of the formula (I)

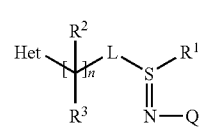

(I)

wherein
Het represents:

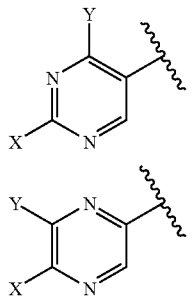 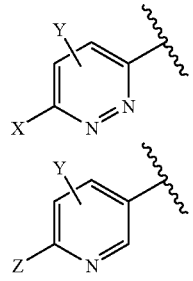

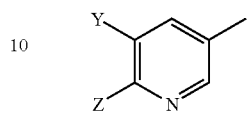

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $COOR^4$, $CONR^4R^5$, or aryl;

Z represents $C_1$-$C_4$ haloalkyl, $C_2$-$C_4$ alkenyl, $C_2$-$C_4$ alkynyl, $C_2$-$C_4$ haloalkenyl, $C_1$-$C_4$ haloalkoxy, CN, $NO_2$, $COOR^4$ or $CONR^4R^5$;

n is an integer from 0-3;

L represents either a single bond or —$CH_2$—;

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, arylalkyl, or, alternatively, $R^2$ and $R^3$ and the common carbon to which they attach form a 3-6 membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloalkenyl, aryl, or arylalkyl;

$R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, or arylalkyl; and Q represents $NO_2$ or CN.

2. A compound of claim 1 in which Q represents CN.

3. A compound of claim 1 in which $R^2$ and $R^3$ independently represent hydrogen or $C_1$-$C_4$ alkyl or $R^2$ and $R^3$ and the common carbon to which they attach form a 3-6 membered ring.

4. A compound of claim 1 in which Het represents

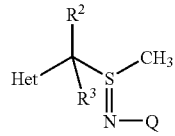

wherein

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $COOR^4$, $CONR^4R^5$, or aryl; and Z represents $C_1$-$C_4$ haloalkyl, $C_2$-$C_4$ alkenyl, $C_2$-$C_4$ alkynyl, $C_2$-$C_4$ haloalkenyl, $C_1$-$C_4$ haloalkoxy, CN, $NO_2$, $COOR^4$ or $CONR^4R^5$.

5. A compound of claim 4 in which Y represents hydrogen and Z represents $C_1$-$C_2$ haloalkyl.

6. A compound of claim 1 having the formula wherein Het, Q, $R^2$ and $R^3$ are as previously defined.

7. A composition for controlling insects which comprises a compound of claim 1 in combination with a phytologically-acceptable carrier.

8. A method of controlling insects which comprises applying to a locus where control is desired an insect-inactivating amount of a compound of claim 1.

\* \* \* \* \*